Figure 1:
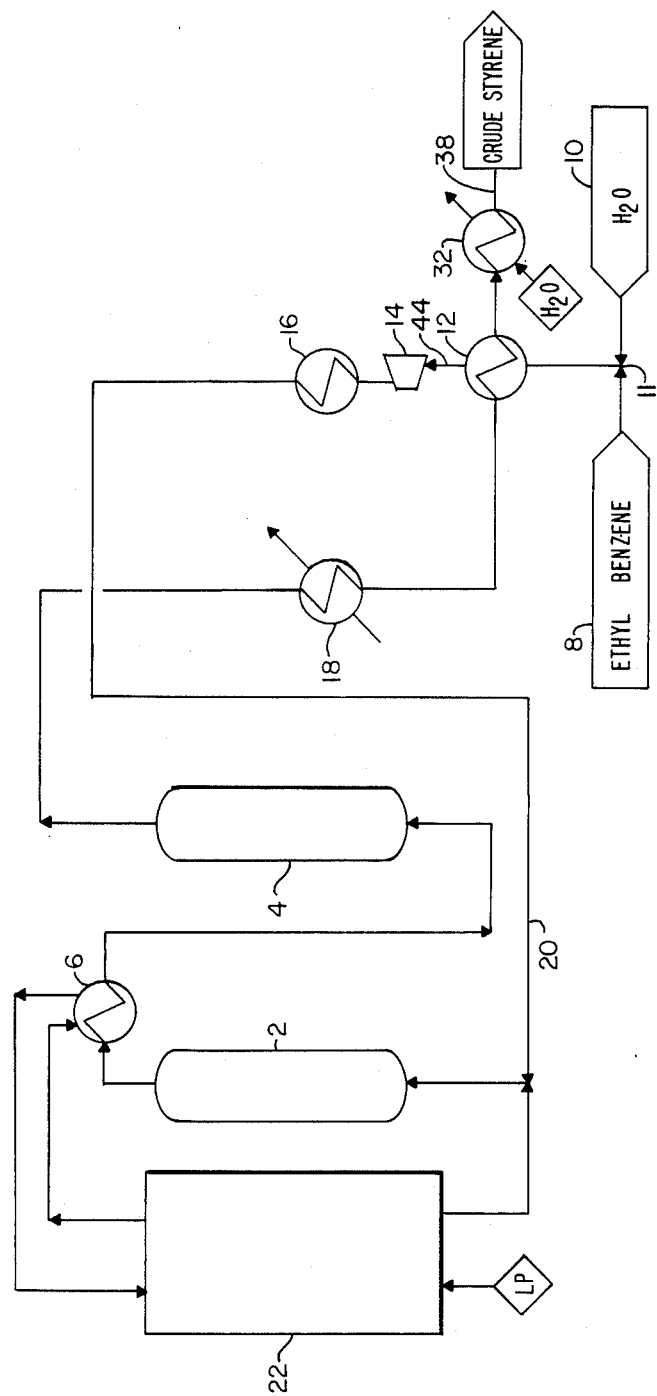

United States Patent [19]

Whittle

[11] Patent Number: 4,695,664

[45] Date of Patent: Sep. 22, 1987

[54] METHOD OF RECOVERING HEAT FROM LOW TEMPERATURE EFFLUENT

[75] Inventor: Leslie F. Whittle, Windham, N.H.

[73] Assignee: The Badger Company, Inc., Cambridge, Mass.

[21] Appl. No.: 853,043

[22] Filed: Apr. 17, 1986

[51] Int. Cl.$^4$ .............................................. C07C 4/02
[52] U.S. Cl. .................................... 585/440; 585/441; 585/442; 585/443; 585/444; 585/445; 585/910
[58] Field of Search ............... 585/440, 441, 442, 443, 585/444, 445, 910

[56] References Cited

U.S. PATENT DOCUMENTS

| | | | |
|---|---|---|---|
| 2,831,907 | 4/1958 | Mayfield et al. | 585/440 |
| 3,515,766 | 6/1970 | Root et al. | 585/910 |
| 3,690,839 | 9/1972 | Jones | 585/440 |
| 3,691,020 | 9/1972 | Hughes | 585/910 |
| 4,338,476 | 7/1982 | Vickers et al. | 585/441 |

Primary Examiner—Curtis R. Davis

Attorney, Agent, or Firm—Schiller, Pandiscio & Kusmer

[57] ABSTRACT

The invention is an improved method and apparatus for recovering waste heat from a low temperature process stream by means of a vaporizable heat sink liquid, characterized by an effective lowering of the boiling temperature of the heat sink liquid without need to reduce its boiling pressure. The heat sink liquid essentially comprises a mixture of two immiscible liquids that form a low boiling azeotrope. The heat sink liquid is brought into indirect heat exchange with the low temperature process stream for heat extraction. The invention involves simultaneous boiling of the two immiscible liquids to suppress the temperature of the heat sink liquid to below the low temperature of the process stream, whereby the heat sink liquid is able to recover heat from the process stream. In a preferred embodiment of the invention, the heat sink liquid comprises the reactants that are fed to a reactor, and the low temperature process stream is the reaction effluent from the reactor.

18 Claims, 3 Drawing Figures

METHOD OF RECOVERING HEAT FROM LOW TEMPERATURE EFFLUENT

This invention relates to the recovery of energy from a low temperature chemical process vapor stream, and more particularly to an improved process for utilizing what would otherwise be waste heat discharged to the atmosphere. The energy is recovered by vaporizing selected liquids for use in the same chemical process or for use as a heat transfer medium to an adjacent process.

BACKGROUND OF THE INVENTION

Since utility costs are a primary factor in the design and operation of plants in the chemical process industries, it is established practice to minimize energy consumption by recovering energy from process or utility gas streams and then recycling the recovered energy to the process (or else using the recovered energy for another purpose). The recovery of energy from a gas stream is achieved by heat exchange with a selected fluid heat sink, e.g., a cooler liquid or gas stream. A typical heat recovery and utilization technique involves heat exchange between a hot reactor effluent gas and water so as to convert the latter to steam, and using the steam as a vehicle for recycling the recovered heat to the reactor.

It is a common occurrence in a chemical plant to have a process or utility gas stream that is at a relatively low temperature but contains more than an insignificant percentage of the energy generated in or supplied to a process. It is desirable to treat the low temperature process or utility gas stream to recover a substantial portion of its energy content. Frequently, however, the energy content is treated as waste heat because its recovery is uneconomical or can be achieved only with difficulty or substantial inconvenience. In this connection, it is to be appreciated that the lower the temperature of the process or utility gas stream, the lower the temperature of the fluid heat sink must be in order for the heat sink to adequately recover energy from the gas stream. One of the problems incurred in attempting to recover energy from a low temperature gas using a liquid heat sink such as water for heat recovery is that the temperature of the heat source, i.e., the process gas stream, may be so low that the liquid heat sink will not boil at a temperature lower than the heat source unless its pressure is lowered. However, if the heated heat sink should constitute a material that is to be fed to another stage of the process operating at a higher pressure, reducing the pressure of the liquid heat sink to enable it to be vaporized by boiling may be undesirable or too costly, since energy must be consumed in compressing the heat sink vapor to the higher pressure desired for the subsequent stage.

SUMMARY OF THE INVENTION

The primary object of this invention is to provide a new and improved method of recovering heat from a relatively low temperature process stream.

A second object of this invention is to provide an improved method of recovering heat from a low temperature process stream by boiling a liquid heat sink.

A more specific object of this invention is to provide an improved method of recovering waste heat from a low temperature process stream by means of a vaporizable liquid heat sink, characterized by an effective lowering of the boiling temperature of the liquid heat sink without need to reduce its boiling pressure.

These and other objects of the invention are achieved by providing a liquid heat sink in the form of a mixture of two immiscible liquids that form a low boiling heterogeneous azeotrope, bringing the liquid heat sink into indirect heat exchange with a low temperature process stream, and using azeotropic boiling of the two immiscible liquids to suppress the temperature of the heat sink liquid, so as to enable the liquid heat sink to recover heat from the low temperature process stream. This invention provides two alternative approaches: (a) if the boiling pressure of the liquid heat sink is fixed by constraints of the chemical process (as where the vaporized heat sink liquid must be fed to a reactor or a distillation column at a predetermined temperature), use of the invention allows the boiling temperature of the liquid heat sink to be reduced to a level permitting heat recovery; and (b) if the boiling temperature of the liquid heat sink is fixed by constraints of the chemical process, the invention makes it possible to maximize the available pressure of the vaporized heat sink.

A primary advantage of the invention is that use of the two phase boiling facilitates energy recovery at a relatively low temperature without necessitating an increase in boiling pressure. A second advantage of the invention is that it maximizes the available pressure of the vaporized heat sink fluid, thus reducing the amount of compression that may be required to achieve a selected pressure level for utilization of the heat sink fluid in a subsequent stage of the process.

The invention has a variety of applications. A preferred emodiment of the invention involves recovery of heat from a reactor effluent by means of a heat sink liquid that comprises a mixture of two immiscible liquids, at least one of which is a feed material for the reaction producing the reactor effluent. By way of example, the invention may be applied to a process system for producing styrene by dehydrogenation of ethylbenzene, in which case the liquid heat sink comprises a mixture of ethylbenzene and water, the feeds for the dehydrogenation reactor. The ethylbenzene/water mixture forms a low boiling azeotrope. The azeotrope is heterogeneous since ethylbenzene and water are not miscible (see J. H. Perry, Chemical Engineers Handbook, 4th Edition, pp. 13-8 to 13-12, McGraw-Hill 1963).

Other features, embodiments and advantages of the invention are described in or rendered obvious by the following detailed description which is to be considered together with the accompanying drawings.

THE DRAWINGS

Figure 2:
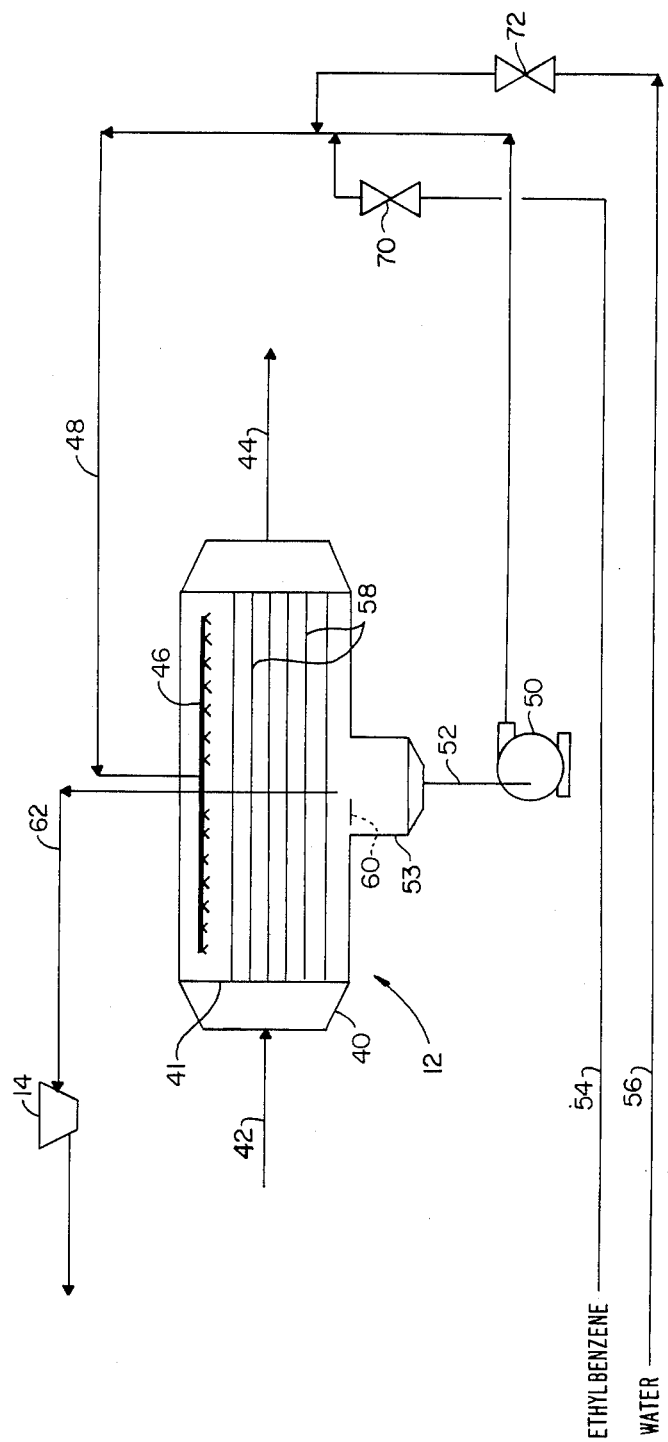
Figure 3:
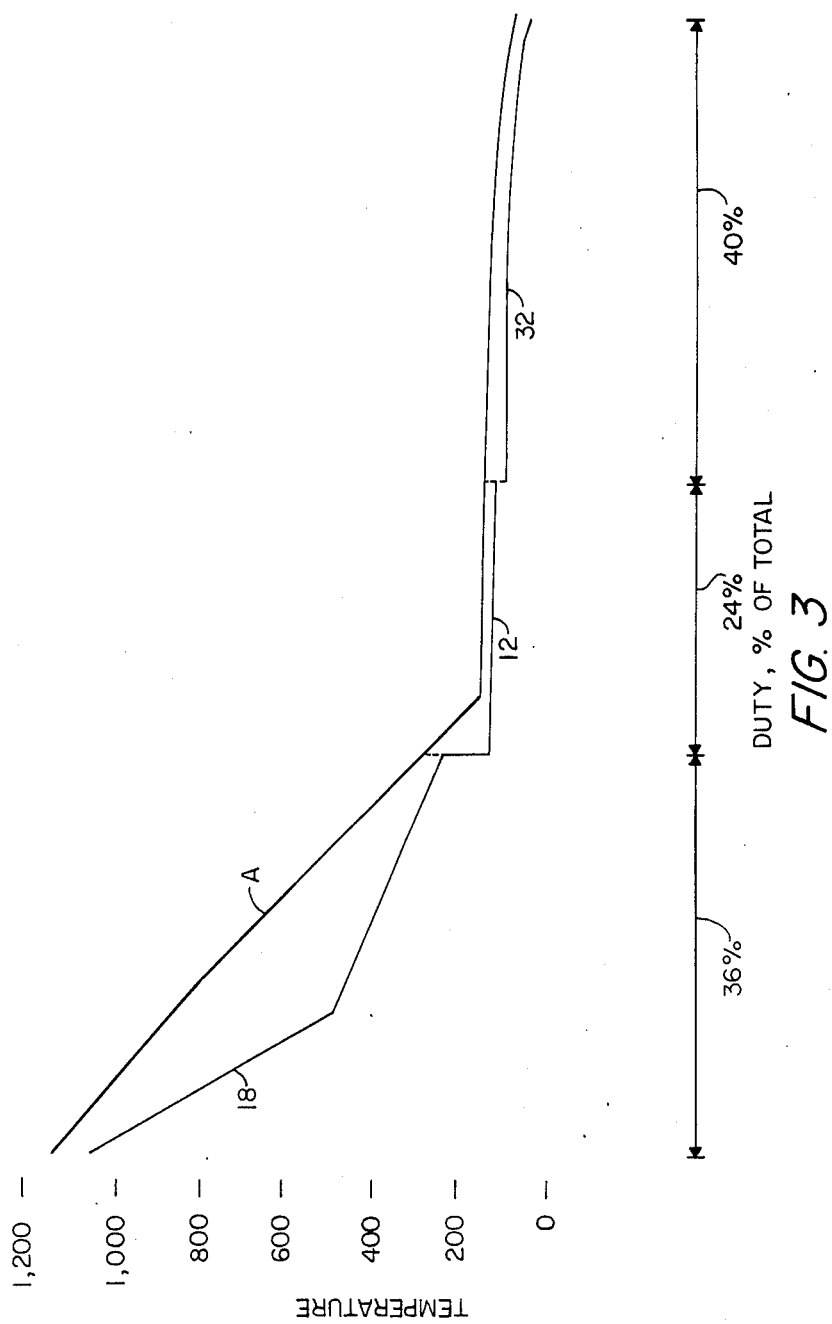

FIG. 1 schematically illustrates the reactor section of a process for the dehydrogenation of ethylbenzene to produce styrene;

FIG. 2 schematically illustrates the feed vaporizer stage of the reactor section;

FIG. 3 is a temperature/heat duty diagram illustrating aspects of the heat recovery operation of the reactor section.

PREFERRED EMBODIMENT OF THE INVENTION

The invention is described in detail hereinafter in relation to its application in a process for the dehydrogenation of ethylbenzene, but it is to be understood that it has other applications, many of which will be obvious to persons skilled in the art.

In a typical ethylbenzene dehydrogenation process known prior to the present invention, the reaction effluent is usually between about 1000 and 1200 degrees F. and comprises unreacted EB, product styrene, steam and light gases. The effluent stream is cooled by indirect heat exchange to usually between 200 and 300 degrees F. in one or more coolers, with the cooling being characterized by extraction of only sensible heat from the effluent stream and no significant condensation of water, EB or styrene. Thereafter, the still vapor-phase effluent stream is then fully desuperheated and partially condensed in a condenser to a temperature of between about 80 and 130 degrees F. to produce a mixed-phase effluent stream. The latter is then treated according to well-known techniques to separate the vapor and liquid phases. Styrene and water are separately recovered from the liquid phase, and the vapor phase is recovered for fuel or other uses.

Because the dehydrogenation reaction of selected hydrocarbon materials such as EB is favorably influenced by a decrease in pressure, prior to this invention it has been generally recommended that commercial hydrocarbon dehydrogenation processes, e.g. dehydrogenation of EB, operate at a relatively low pressure in order to achieve satisfactory hydrocarbon conversion. However, in the 1983-1984 time frame, commercial operations have usually employed a pressure in the dehydrogenation zone which is between one half to one and one half atmospheres pressure.

Dehydrogenation conditions in general for ethylbenzene (and homologs and analogs thereof) include a reaction temperature in the reactor(s) in the range of about 950 degrees F. to approximately 1300 degrees F., preferably about 1050 degrees F. The pressure within the dehydrogenation reactor(s) typically ranges from about 400 mm Hg to about 1200 mm Hg absolute. The operating pressure within the dehydrogenation reactor(s) is measured at the inlet, midsection and outlet section of the reactor(s) to thereby provide an appropriate average pressure.

It is preferred that the ratio of steam to ethylbenzene or other alkylaromatic feedstock range from about 0.8 lbs to about 2.0 lbs of steam per pound of feedstock, or a ratio of between about 5:1 to 12:1 on a mole basis.

The effluent from the dehydrogenation reactor section typically contains less than about 3 lbs steam per pound of hydrocarbon product.

The foregoing dehydrogenation conditions are observed in the practice of this invention.

The present invention is arranged to make use of the fact that certain immiscible liquids form an heterogeneous azeotrope when brought together, with the azeotrope having a boiling point that is lower than the boiling points of the individual liquids at the same pressure. Water and ethylbenzene form such an heterogeneous azeotrope, as explained in greater detail hereinafter.

Referring now to FIG. 1, there is illustrated a dehydrogenation reactor section of an ethylbenzene dehydrogenation process arranged to take advantage of the present invention. The system shown in FIG. 1 comprises "A" and "B" reactors 2 and 4, with the effluent from reactor 2 being fed to reactor 4 via a reheater 6. The feeds to reactor 2 comprise ethylbenzene ("EB") vapor and steam.

Ethylbenzene and water are delivered as liquids from sources of supply 8 and 10 and are mixed at 11 to form a dilute EB feed stream for delivery to a vaporizer 12 that consists of a heat exchanger constructed as described hereinafter in connection with FIG. 2. The ethylbenzene and water feed stream is vaporized in vaporizer 12 and then fed to a compressor 14 where it is compressed to a pressure somewhat higher than the level of the operating pressure of reactors 2 and 4 before passing on to one or more heating heat exchangers (and/or furnaces) 16 where it is heated to a selected temperature suitable for it to be introduced to reactor 2 via a line 20. The dilute ethylbenzene feed stream in line 20 is diluted further with superheated steam delivered from a steam superheater 22 as it is fed into reactor 2. In reactor 2, at least some of the EB is dehydrogenated to styrene.

The gaseous effluent from the reactor 2, comprising primarily unreacted EB, steam, and styrene, is heated in reheater 6 by heat exchange with steam from superheater 22 (or via an alternative heat source) to a selected temperature suitable for it to be introduced to the "B" reactor 4. Additional EB in the effluent from "A" reactor 2 is dehydrogenated in "B" reactor 4, and then the effluent from reactor 4 undergoes sensible heat cooling in one or more heat exchangers 18 by exchange of heat with water, organic feed or other suitable liquids. Although not shown, it is to be understood that steam superheater 22 includes heat supply means, e.g., a gas burner, for superheating the low pressure steam.

After passing through one or more sensible heat coolers 18, the still vapor-phase reactor effluent passes through vaporizer 12 where it gives up heat by vaporizing the water/EB feed. Thereafter the effluent, in partially condensed form, passes through a further heat exchanger 32 which is cooled with water and functions as a condenser to liquify the styrene component of the effluent. The reactor effluent stream recovered from condenser 32 is a mixed phase (liquid/vapor) crude styrene stream 38. That stream is processed in other equipment (not shown), according to well known techniques, to recover a nearly pure styrene product.

Referring now to FIG. 2, feed vaporizer 12 is in the form of a horizontal spray film evaporator, comprising a vessel 40 having a shell and tube type heat exchanger 41 and inlet and outlet lines 42 and 44, whereby cooled reactor effluent may be passed through the tubes 58 of the shell and tube heat exchanger. On the shell side, a liquid spray head 46 is connected to a line 48 that in turn is connected via a circulating pump 50 to a drain line 52 in a sump section 53 of vessel 40. The liquid EB and water supplies are connected to line 48 via lines 54 and 56 and suitable flow-control valve means 70 and 72 respectively. Ethylbenzene and water in feed lines 54 and 56 mix with recirculated liquid delivered via pump 50 and are sprayed over tubes 58 of the shell and tube section of the vessel 40 by means of spray head 46. The solid line 60 in FIG. 2 indicates the normal liquid level in the sump 53 of vessel 40. In vessel 40, EB is vaporized and water is converted to steam by exchange of heat with the condensing reactor effluent flowing in tubes 58. The vaporized EB and steam are removed from vessel 40 via a line 62 which leads to the reactor feed compressor 14.

The ethylbenzene/water azeotrope has an azeotropic boiling temperature below the boiling point of the more volatile component, i.e., water, of the azeotrope mixture. More specifically, an EB/water mixture is azeotropic and boils between 140 to 170 degrees F. at a pressure of between 4 to 8 psia. That mixture is azeotropic at approximately 2.6 moles of water to approximately 1 mole of ethylbenzene.

As a consequence, if (1) an EB/water mixture containing at least 2.6 moles of water for each mole of EB is introduced to vaporizer 12 via line 42 and sprayed via spray head 46 into contact with tubes 58 at a pressure of about 4 psia, and (2) tubes 58 are at a temperature above 140 degrees F., the mixture will be heated to 140 degrees F. or above and, as a consequence, EB and water will boil off at about 140 degrees F. in a mole ratio of about 1 to 2.6.

FIG. 3 illustrates simultaneously (a) the temperature profile of an ethylbenzene dehydrogenation reactor effluent as it undergoes cooling according to a preferred embodiment of the present invention in the several stages of the reactor section illustrated in FIGS. 1 and 2, and (b) the mode of utilization of the heat recovered from the gaseous effluent.

With reference to FIG. 3, the upper solid line curve A represents the temperature of the reactor effluent. The lower solid line curve shows the energy recovered from the reactor effluent. The dehydrogenation reaction effluent is at a temperature of about 1000 degrees F. or higher as it passes out of the dehydrogenation reactor 4. In sensible heat cooler(s) 18, the gaseous effluent is cooled by conventional heat recovery methods to a temperature between 200 and 300 degrees F. In vaporizer 12 the gaseous effluent is cooled further and partially condensed at a temperature of approximately 160 to 200 degrees F. by exchange of heat with the ethylbenzene/water mixture, causing the latter to be vaporized. In condenser 32 the mixed-phase effluent stream 38 is cooled and condensed further to a temperature of between about 80 and 130 degrees F., with the styrene being one of the components that is condensed.

Having water present in vaporizer 12 in excess of the amount required for the azeotrope is desirable in providing adequate wetting of the tube surface for efficient heat transfer for vaporizing the azeotropic mixture. Therefore, in practicing this invention it is preferred that the water feed to the system be sufficient to assure that the proportion of water in the water/EB mixture in vaporizer 12 exceed the proportion of water in the azeotrope, so as to assure adequate heat transfer and achieve adequate boiling in the vaporizer.

As used herein the terms "dehydrogenation reactor section" is intended to include the entire reaction zone (which may comprise a single catalyst-containing reactor, two catalyst-containing reactors as shown in FIG. 1, or three or more more catalyst-containing reactors), plus means for heating the reactor feed and recovering heat from the reactor effluent. The catalyst may be divided into a plurality of beds, one or more in each reactor. The dehydrogenation catalysts may take various forms but preferably they consist of one or more metallic components selected from Groups VI and VIII of the Periodic Table. Typical catalysts for the dehydrogenation of alkylaromatics are set forth in U.S. Pat. No. 4,779,025, issued Oct. 23, 1984 to UOP INC. for Alkylaromatic Hydrocarbon Dehydrogenation Process. Different hydrogenation catalysts may be used in different beds as described in U.S. Pat. No. 3,223,743.

The invention obviously is applicable to dehydrogenation reactions involving analogs or homologs of ethylbenzene, e.g., the dehydrogenation of para-ethyltoluene or diethylbenzene. Still other possible applications of the invention include, but are not limited to, steam reforming in the production of synthesis gas. The invention also may involve reactors operating at pressures and feed mole ratios other than those commonly used in the art.

It also is to be appreciated that the invention is not limited to use of horizontal film spray evaporators for the azeotropic vaporization of the organic/water reactants, e.g. eb and water, and that other forms of vaporizing equipment may be used for that purpose.

Following is a specific example of the invention as embodied in a process as illustrated in FIGS. 1 and 2 for the manufacture of styrene using ethylbenzene and water as the feed materials.

SPECIFIC EXAMPLE

Liquid ethylbenzene and water are fed continuously from sources of supply 8 and 10 respectively to the spray head 46 of vaporizer 12 together with water recirculated from vaporizer 12. The flow rates in lines 54, 56 and 52 are set so that the stream delivered to spray head 46 comprises water and EB in a ratio of about 2.6 to 1 moles. The liquid fed to spray head 46 is at a temperature of about 140 to 150 degrees F. and at a pressure of about 14 to 18 psia. In vaporizer 12 the EB/water mixture is heated to a temperature of between about 140 to 170 degrees F., with the result that the water and EB are vaporized in a mol ratio of about 2.6 to 1.0. Thereafter the EB/steam vapor in line 62 of vaporizer 12 is compressed by compressor 14 to a pressure of about 20 to 30 psia. Then the compressed vapor stream is heated in exchanger(s) 16 from a temperature of about 330 to 290 degrees F., to a temperature in the range of 1000 to 1050 degrees F. The vapor stream is then mixed with superheated steam from superheater 22 in the ratio of about 4.6 moles of EB/water mixture to about 6.4 moles of superheated steam, and the resulting mixture is delivered to the "A" reactor 2. The latter is operated at an inlet pressure of about 11 to 15 psia and an inlet temperature of about 1100 to 1150 degrees F.

The effluent from reactor 2 leaves the reactor at a temperature of about 1000 to 1050 degrees F. and is heated to a temperature of about 1125 to 1175 degrees F. in reheater 6 before passing into the "B" reactor 4. The effluent from reactor 4 is at a temperature of about 1050 to 1100 degrees F. and a pressure of about 8 to 12 psia when it passes to sensible heat cooler(s) 18 where it is cooled to a temperature of about 280 degrees F.

Next the effluent is cooled to a temperature of about 155 to 185 degrees F. in vaporizer 12, after which styrene is further liquified by cooling the effluent to a temperature of about 90 degrees F. in condenser 32. From condenser 32 the partially liquified effluent stream 38 is passed to other equipment (not shown) for separation and recovery of a nearly pure styrene product, water, hydrocarbon by-products, and unreacted EB.

Additionally, a most efficient heat recovery is achieved as the effluent is cooled from a temperature in excess of 1050 degrees F. as it enters heat recovery exchanger(s) 18 to a temperature of about 90 degrees F. as it leaves condenser 32, with the recovered heat being utilized approximately as follows: 36% for heat recovery in exhanger(s) 18, 24% for vaporizing the EB/water mixture in vaporizer 12, and 40% in heating cooling water in condenser 32. The water heated in condenser 32 may be fresh and/or reused water, and may be utilized as the water supply for the reactors.

The foregoing example demonstrates that a significant percentage (about 24%) of the recovered heat is recovered at a low temperature, but in a manner that is highly beneficial since it is used to vaporize the EB feed.

Of course, the invention is not limited in its application to a styrene manufacturing process conducted as hereinabove described, since the process operating conditions may be varied in ways well known to persons skilled in the art without adversely affecting the heat recovery advantages of the invention. Furthermore, the invention may be adapted to recover heat from other reaction effluents using a reactant-containing low boiling azeotrope as the heat sink liquid.

What is claimed is:

1. A process for the dehydrogenation of an alkylaromatic hydrocarbon which comprises the steps of:
   (a) continuously contacting a reactant vapor stream comprising an alkylaromatic hydrocarbon and steam with a dehydrogenation catalyst in a reactor under dehydrogenation conditions so as to form a vapor phase dehydrogenation reaction effluent comprising a predetermined product hydrocarbon;
   (b) continuously removing said effluent as a stream from said reactor;
   (c) continuously mixing an alkylaromatic hydrocarbon and water in liquid form so as to form an azeotropic feed mixture;
   (d) cooling said effluent stream without any significant condensation of said predetermined product hydrocarbon by indirect heat exchange with a selected fluid cooling medium;
   (e) recovering additional heat from said effluent stream by indirect heat exchange with said azeotropic feed mixture so as to cause vaporization of said alkylaromatic hydrocarbon and water; and
   (f) feeding said vaporized alkylaromatic hydrocarbon and water to said reactor as said reactant vapor stream.

2. A process according to claim 1 wherein said effluent stream is cooled in step (d) to a temperature of about 280 degrees F.

3. A process according to claim 1 wherein said effluent stream is cooled in step (d) by indirect heat exchange with said vaporized alkylaromatic hydrocarbon and water.

4. A process according to claim 1 wherein said alkylaromatic hydrocarbon is ethylbenzene.

5. A process according to claim 1 wherein said predetermined product hydrocarbon is an unsaturated hydrocarbon.

6. A process according to claim 5 wherein said unsaturated hydrocarbon is styrene.

7. A process for the dehydrogenation of an alkylaromatic hydrocarbon which comprises the steps of:
   (a) continuously contacting a reactant vapor stream comprising an alkylaromatic hydrocarbon and steam with a dehydrogenation catalyst in a reactor under dehydrogenation conditions so as to form a vapor phase dehydrogenation product hydrocarbon;
   (b) continuously removing said effluent as a stream from said reactor;
   (c) continuously mixing an alkylaromatic hydrocarbon and water in liquid from so as to form a heterogeneous azeotropic liquid feed mixture;
   (d) recovering sensible heat from said effluent stream without any significant condensation of said dehydrogenation product hydrocarbon by subjecting said effluent stream to indirect heat exchange with a selected fluid material;
   (e) recovering latent heat from said effluent stream by subjecting said effluent stream to indirect heat exchange with said azeotropic feed mixture so as to cause condensation of a significant quantity of said dehydrogenation product hydrocarbon and vaporization of said alkylaromatic hydrocarbon and water, said effluent stream being cooled by the recovery of latent heat to a temperature near or below the atmospheric boiling point of water;
   (f) feeding said vaporized alkylaromatic hydrocarbon and water to said reactor as said reactant vapor stream; and
   (g) cooling said reactor effluent further by subjecting it to indirect heat exchange with a fluid cooling medium so as to cause condensation of an additional quantity of said dehydrogenation product hydrocarbon.

8. A process for producing a selected organic compound which comprises the steps of:
   (a) continuously contacting a reactant vapor stream comprising at least first and second selected reactants with a selected catalyst in a reactor under predetermined reaction conditions so as to form a vapor phase reaction effluent comprising said selected organic compound;
   (b) continuously removing said effluent as a stream from said reactor;
   (c) continuously mixing said first and second selected reactants in the liquid state so as to form an azeotropic liquid feed mixture;
   (d) recovering sensible heat from said effluent stream without any significant condensation of said selected organic compound by subjecting said effluent to indirect heat exchange with a selected fluid material;
   (e) thereafter recovering latent heat from said effluent stream by subjecting said stream to indirect heat exchange with said azeotropic feed mixture so as to cause condensation of a significant quantity of said organic compound in said stream and vaporization of said first and second reactants in said feed mixture; and
   (f) feeding said vaporized first and second reactants together to said reactor as said reactant vapor stream.

9. A process for producing styrene from ethylbenzene comprising the following steps:
   (a) continuously contacting a reactant vapor feed stream comprising ethylbenzene and steam with a dehydrogenation catalyst in a reactor under dehydrogenation conditions so as to form a reaction effluent comprising styrene in the vapor phase;
   (b) continuously removing said effluent from said reactor at a temperature of at least about 1000 degrees F.;
   (c) continuously mixing ethylbenzene and water in liquid form so as to form a heterogeneous azeotropic liquid feed mixture;
   (d) recovering sensible heat from said effluent without any significant condensation of styrene by subjecting said effluent to indirect heat exchange with a selected material, said effluent being cooled by said sensible heat recovery to a temperature of between about 200 and 300 degrees F.;
   (e) thereafter recovering latent heat from said effluent by subjecting said effluent to indirect heat exchange with said azeotropic feed mixture so as to cause condensation of a significant portion of the styrene component of said effluent and vaporization of the ethylbenzene and water components of said azeotropic feed mixture; and (f) feeding the vaporized ethylbenzene and water components of said azeotropic feed mixture to said reactor as said reactant vapor feed stream.

10. A process according to claim 9 wherein said effluent is cooled in step (e) to a temperature of between about 155 and 185 degrees F.

11. A process according to claim 10 wherein in step (e) said ethylbenzene and water components are heated to a temperature of between about 140 and 170 degrees F.

12. A process according to claim 11 wherein in step (d) said azeotropic feed stream contains at least 2.6 moles of water for each mole of ethylbenzene.

13. A process according to claim 9 wherein said reactor is operated at an inlet pressure of between about 11 and 15 psia.

14. A process according to claim 13 wherein said reactant vapor feed stream is compressed to a pressure greater than said inlet pressure between steps (e) and (f).

15. A process according to claim 13 wherein said reactant vapor feed stream is compressed to a pressure of between about 20 and 30 psia and heated to a temperature of about 1000 degrees F. or higher between steps (e) and (f).

16. A process according to claim 9 wherein step (e) is conducted in a spray film evaporator having a shell and tube type heat exchanger.

17. A process according to claim 16 wherein said reactor effluent is passed through the tubes of the shell and tube type heat exchanger, and the water and ethylbnzene in said liquid feed mixture are sprayed onto said tubes in a ratio of at least about 2.6 moles of water for each mole of ethylbenzene, and water and ethylbenzene are vaporized by absorption of heat from said effluent via said tubes.

18. A process according to claim 9 wherein said azeotropic feed mixture comprises at least about 2.6 moles of water for each mole of ethylbenzene.

* * * * *